United States Patent [19]

Apple

[11] 4,257,266
[45] Mar. 24, 1981

[54] SAMPLE EXTRACTOR

[76] Inventor: Clarence L. Apple, 381 Albany, Shreveport, La. 71105

[21] Appl. No.: 19,775

[22] Filed: Mar. 12, 1979

[51] Int. Cl.³ .............................................. E21B 47/00
[52] U.S. Cl. ..................................... 73/155; 73/421 B
[58] Field of Search ..................... 73/155, 151, 421 B, 73/422 R; 166/264

[56] References Cited

U.S. PATENT DOCUMENTS

| | | | |
|---|---|---|---|
| 3,924,471 | 12/1975 | Singer | 73/421 B |
| 4,022,059 | 5/1977 | Schontzler | 73/421 B X |

Primary Examiner—Jerry W. Myracle

[57] ABSTRACT

An automatic extractor of capsuled oil well drilling fluid samples and a process for extracting the fluid samples, the extractor including a vertically oriented tube canister for storing a quantity of empty sample capsules; a plate canister which contains a supply of plates for storing the filled sample capsules; a pivotally mounted sampling device positioned between the tube canister and the plate canister, which sampling device operates to remove the sample capsules one by one from storage in the tube canister, immerse the capsules in a stream of drilling fluid from which a sample is desired, and insert the filled sample capsule in the plate canister; and a plate conveyor in cooperation with the plate canister for periodically removing filled plates containing the sealed capsules and samples.

17 Claims, 36 Drawing Figures

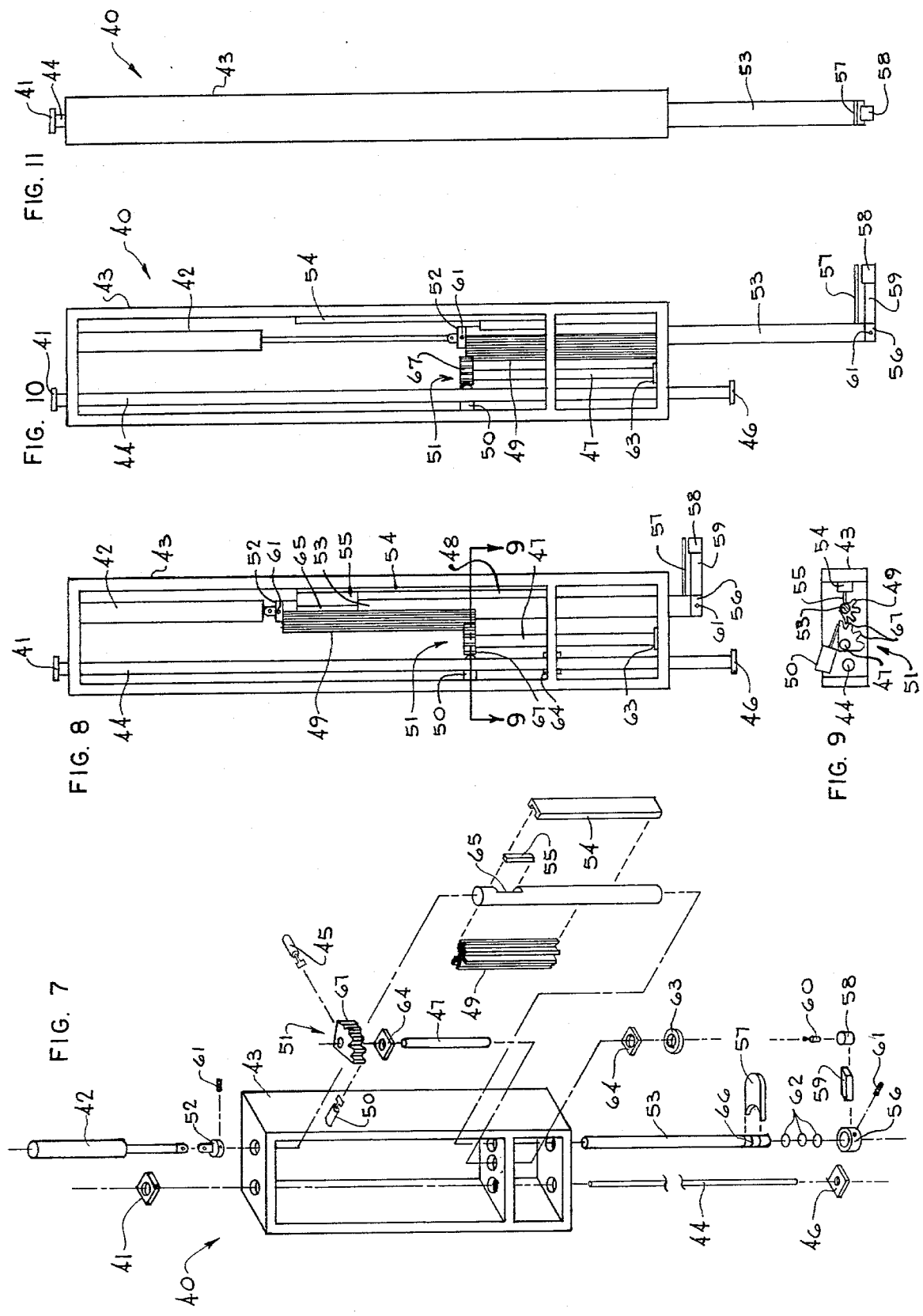

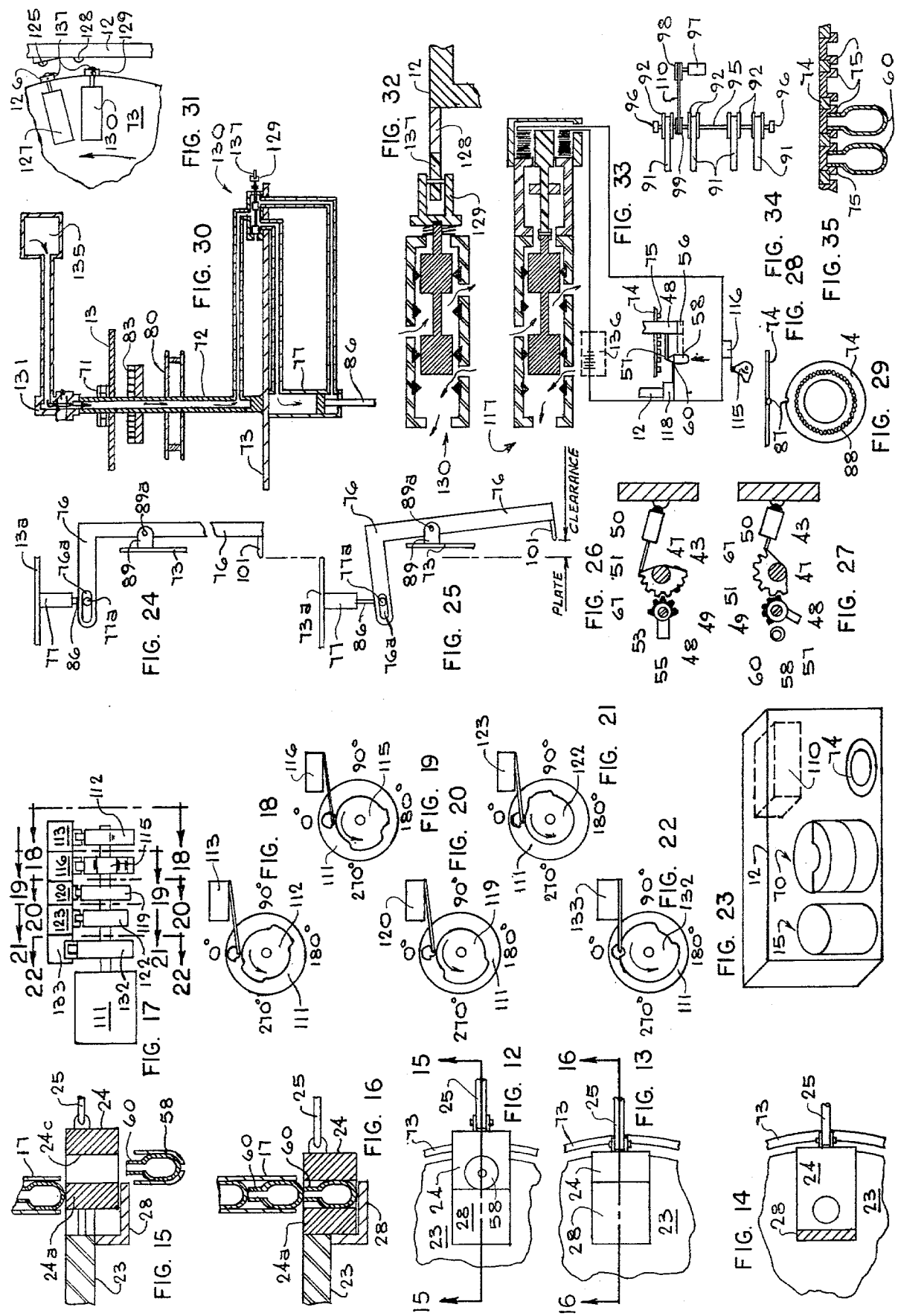

SAMPLE EXTRACTOR

BACKGROUND OF THE INVENTION

1. Field of the Invention

This invention relates to automatic extraction of capsuled samples of fluid, and more particularly, to the automatic and periodic extraction of capsuled samples of oil well drilling fluids during the course of drilling oil and gas wells. The analysis of oil and gas well drilling fluid in order to determine the amount and kind of hydrocarbon components entrained in the fluid during the course of drilling is of prime concern to those who are involved in "mud logging" of drilled wells. For many reasons pertinent to the drilling operation it is important to obtain an accurate, quantitative measurement of hydrocarbons contained in the drilling fluid at the time the drill bit penetrates a particular stratum or interval under measurement. Not only is it important to compile this information when the well is being drilled, but it is also desirable to maintain a sealed, representative sample of the drilling fluid which can be stored and used in subsequent analysis for future reference. Furthermore, it is important to obtain such capsuled samples over a relatively long time period on an automated basis in order to provide an accurate and inexpensive log of the drilling operation.

2. Description of the Prior Art

In mud logging operations undertaken pursuant to the drilling of an oil or gas well, the gas trap or extractor in the mud pumping system is normally located at the shale shaker. A portion of the pumped drilling fluid is diverted through the gas trap to effect release of all or part of the hydrocarbons or other gases entrained in the drilling fluid, and the resulting gas-air mixture is continually drawn from the trap through a hose to the mud logging unit. At this unit the mixture is analyzed on a continuous basis by means of a hot wire detector, or by batch methods using such techniques as gas chromotography, hydrogen flame detection, or mass spectroscopy, and the amount of gas in the fluid is observed and recorded. Normally, there is no method for storing the samples so tested for later examination, and no known substantive method presently exists to prove whether any gas was, in fact, present in the drilling fluid under circumstances where the trap malfunctions and no gas is extracted. Under such circumstances, it is generally assumed that no gas was present in the drilling fluid and the results are so recorded. Furthermore, the conventional gas trap technique of extracting hydrocarbons and other gases in the drilling mud are frequently limited by the physical properties of the drilling fluid and mud pumping system in terms of physically locating the trap in the system for continuous and efficient operation.

Accordingly, it is an object of this invention to provide a new and improved process and apparatus for extracting encapsulated samples of oil and gas well drilling fluid from which a complete and periodic hydrocarbon or other gas analysis can be made either at the time of extraction or in the future.

It is a further object of this invention to provide an oil and gas well drilling fluid sample extracting apparatus which is mounted between the bell nipple and the shale shaker in the drilling rig and functions to trap and encapsulate samples of the drilling fluid pumped between the bell nipple and the shale shaker screen for current or future analysis.

Another object of this invention is to provide a sampling apparatus and procedure which are capable of automatically providing multiple capsules and encapsulated samples from a stream of oil or gas well drilling fluid on a periodic basis by extracting empty capsules from a storage container, immersing the capsules in a stream of the drilling fluid to be tested and storing the capsules in sealed condition for immediate or subsequent analysis.

Yet another object of this invention is to provide a method and apparatus for providing sealed capsules containing drilling fluid samples which may be chronologically stored in order that at some future time a specified drilling fluid sample or samples may be identified as to the time, date and depth of drill penetration which occurred when the oil or gas well was drilled.

A still further object of this invention is to provide a method and apparatus for extracting samples of oil and gas well drilling fluid on a continuous basis without the necessity of interrupting any of the drilling operations.

Another object of the invention is to provide a method and apparatus for securing sealed, encapsulated samples of oil or gas well drilling fluid on a periodic basis and automatically, in such a manner as to permit identification of each capsule sample with the depth of the drill bit penetration, thus identifying the strata or interval from which the particular sample in question originated.

Still another object of the invention is to provide an apparatus and method which is capable of producing multiple, encapsulated samples of drilling fluid or mud on an extended time basis, thus creating data for the production of the log of the well such that the resulting log provides meaningful information as to the well characteristics.

Yet another object of the invention is to provide a method and apparatus for securing capsule samples of drilling fluid from which a quantitative measurement of hydrocarbons and other gases in the drilling fluid can be determined relative to the amount of hydrocarbons entering the fluid at the time the drill bit penetrated a particular interval or strata under measurement.

SUMMARY OF THE INVENTION

These and other objects of the invention are provided in an automatic drilling fluid sample extractor apparatus which is characterized by a vertically oriented, multiple tube or cell tube canister for storing a quantity of empty sample capsules; a cylindrically shaped plate canister containing multiple plates for storage of filled capsules; a sampling apparatus pivotally positioned between the tube canister and plate canister and adapted to automatically remove sample capsules from the tube canister, immerse the capsules in the drilling fluid stream, and place the capsules in the bottom one of the plates positioned in the plate canister; and a plate conveyor disposed beneath the plate canister and designed to remove the filled plates containing the encapsulated samples from the plate canister to a storage or analysis area.

Another aspect of the invention relates to a process for securing the above described encapsulated samples, the process generally including the following steps:

1. Loading a supply of empty sample capsules in a tube canister;
2. Removing the sample capsules individually from the tube canister;

3. Immersing the sample capsules individually in a stream of drilling fluid for a selected period of time to effect filling of the capsules;

4. Sealing the capsules while the capsules are immersed in the fluid stream;

5. Removing the sealed capsules from the fluid stream; and

6. Sequentially storing the sealed capsules for future analysis.

BRIEF DESCRIPTION OF THE DRAWINGS

This invention will be better understood by reference to the accompanying drawings, wherein:

FIG. 7 is an exploded view of the sampler unit in the sample extractor;

FIG. 8 is a front elevation of the sampler illustrated in FIG. 7, with the capsule mechanism in retracted position;

FIG. 9 is a sectional view taken along lines 9—9 of the sampler illustrated in FIG. 8;

FIG. 10 is a front elevation of the sampler illustrated in FIG. 7, with the capsule mechanism in extended configuration;

FIG. 11 is a right side elevation of the sampler illustrated in FIG. 7 with the capsule mechanism in extended configuration;

FIG. 12 is a bottom elevation, partially in section, of the capsule retainer and cage mechanism with the capsule gate open;

FIG. 13 is a bottom elevation, partially in section, of the capsule retainer and cage mechanism with the capsule gate closed;

FIG. 14 is a bottom elevation, partially in section, of the capsule retainer and capsule gate mechanism with the bottom section of the capsule retainer removed;

FIG. 15 is a side sectional view, taken along lines 15—15 in FIG. 12, of the capsule retainer and gate with a capsule in position in the cage;

FIG. 16 is a side sectional view, taken along lines 16—16 in FIG. 13 of the capsule retainer and gate with a capsule in position inside the gate;

FIG. 17 is a side elevation of a timing motor and cooperating mechanism for operation of the sampler;

FIG. 18 is a sectional view taken along lines A—A' in FIG. 17, of the sampler cam in the timing motor mechanism;

FIG. 19 is a sectional view, taken along lines B—B' in FIG. 17, of the seal cam in the timing motor mechanism;

FIG. 20 is a sectional view, taken along lines C—C' in FIG. 17, of a frame cam in the timing motor mechanism;

FIG. 21 is a sectional view taken along lines D—D' in FIG. 17, of the ratchet cam in the timing motor mechanism;

FIG. 22 is a sectional view taken along lines E—E' in FIG. 17, of the capsule gate cam in the timing motor mechanism;

FIG. 23 is a pictorial illustration of the sample extractor and housing or cabinet locating the sample extractor command center;

FIG. 24 is a side elevation, partially in section, of the plate canister shell and plate release mechanism in closed position;

FIG. 25 is a side elevation, partially in section, of the plate canister shell and plate release mechanism in extended or open configuration;

FIG. 26 is a sectional view of the seal mechanism of the sampler illustrated in FIGS. 7—11, which functions to position the seal in closed position;

FIG. 27 is a sectional view of the seal mechanism of the sampler which functions to position the seal in open position;

FIG. 28 is a side elevation of a plate for storing filled samples;

FIG. 29 is a top elevation of the plate illustrated in FIG. 28;

FIG. 30 is a side sectional view of the plate release mechanism of the plate canister;

FIG. 31 is a top elevation, partially in section, of the plate release cam and operator in the plate canister;

FIG. 32 is a sectional view of the plate release cam and operator in the plate canister;

FIG. 33 is a sectional view of the seal solenoid valve;

FIG. 34 is a side elevation, partially in section, of a pulley system in the plate conveyor;

FIG. 35 is a sectional view of a plate for storing filled samples, more particularly illustrating two sample capsules positioned therein.

DESCRIPTION OF THE PREFERRED EMBODIMENTS

Figure 2:
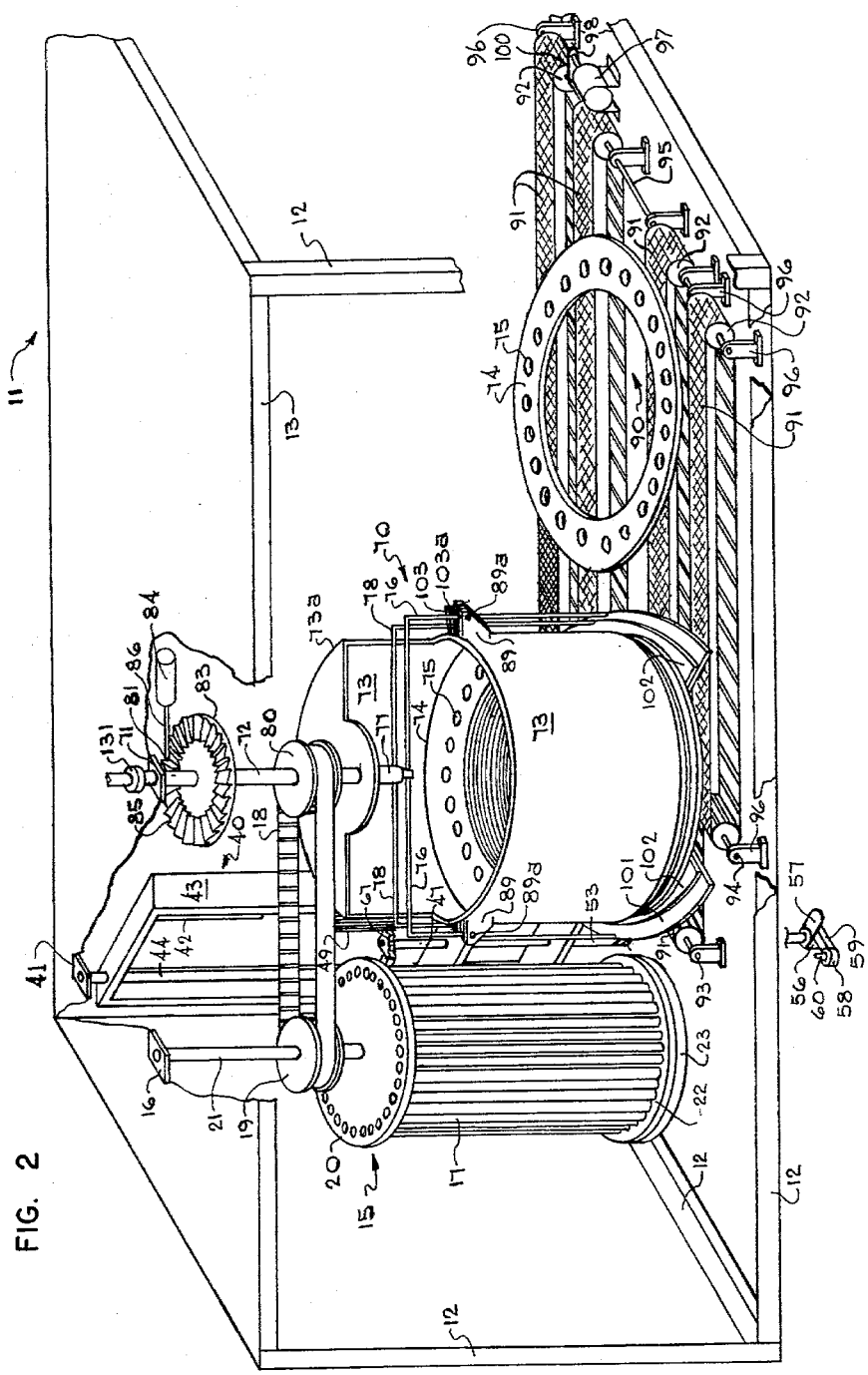
FIG. 2 is a perspective view, partially in section, of the sample extractor enclosed in a cabinet or housing.

Referring to FIG. 2 of the drawings, the sample extractor of this invention is generally indicated by reference numeral 11, and includes the following components: a tube canister 15, the primary function of which is the storage and transfer of empty capsules 60 to the cage 58 of the sampler 40; a sampler 40, designed to secure a drilling fluid sample by submerging one of capsules 60 in a stream of drilling fluid, removing the rotating seal 57 while the capsule is submerged, allowing the fluid to enter the capsule, and finally, closing the seal 57 before the capsule is withdrawn from the fluid. Sampler 40 also functions to transfer the sealed capsule from the cage 58 to a plate 74, positioned in plate canister 70 and fitted with a plurality of caps 75, to seal capsules 60 during storage; a plate canister 70, for receiving and storing the capsules 60 after the capsules are filled with drilling fluid. When each plate 74 is filled with capsules while in the bottom plate position in plate canister 70, the plate is transferred to a plate conveyor 90, and a new plate 74 moves into position to receive additional capsules 60 as the capsules are continually filled with drilling fluid; and a plate conveyor 90, which receives each filled plate 74 and moves it to a remote location for eventual removal, an operation which clears the area under plate canister 70 for the next filled plate 74 to be released.

Figure 1:
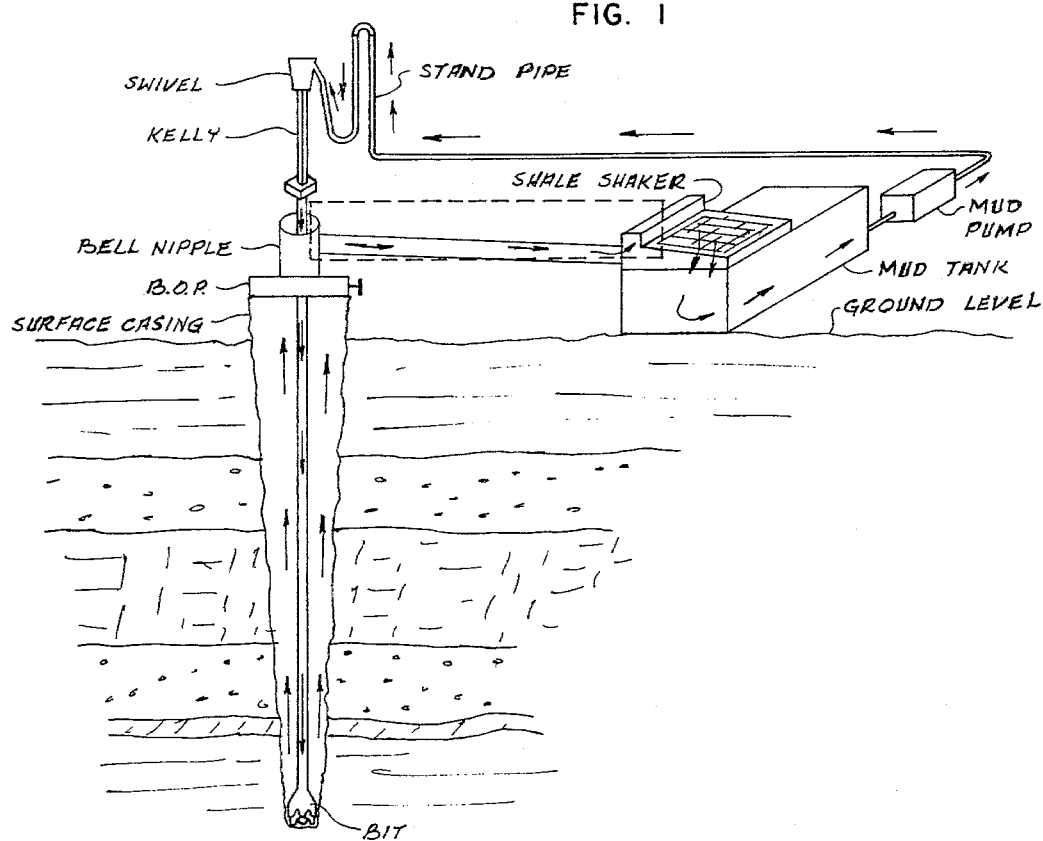
FIG. 1 is a perspective view, partially in section, illustrating a typical well and a preferred placement of the sample extractor of this invention relative to the well location.
Figure 3:
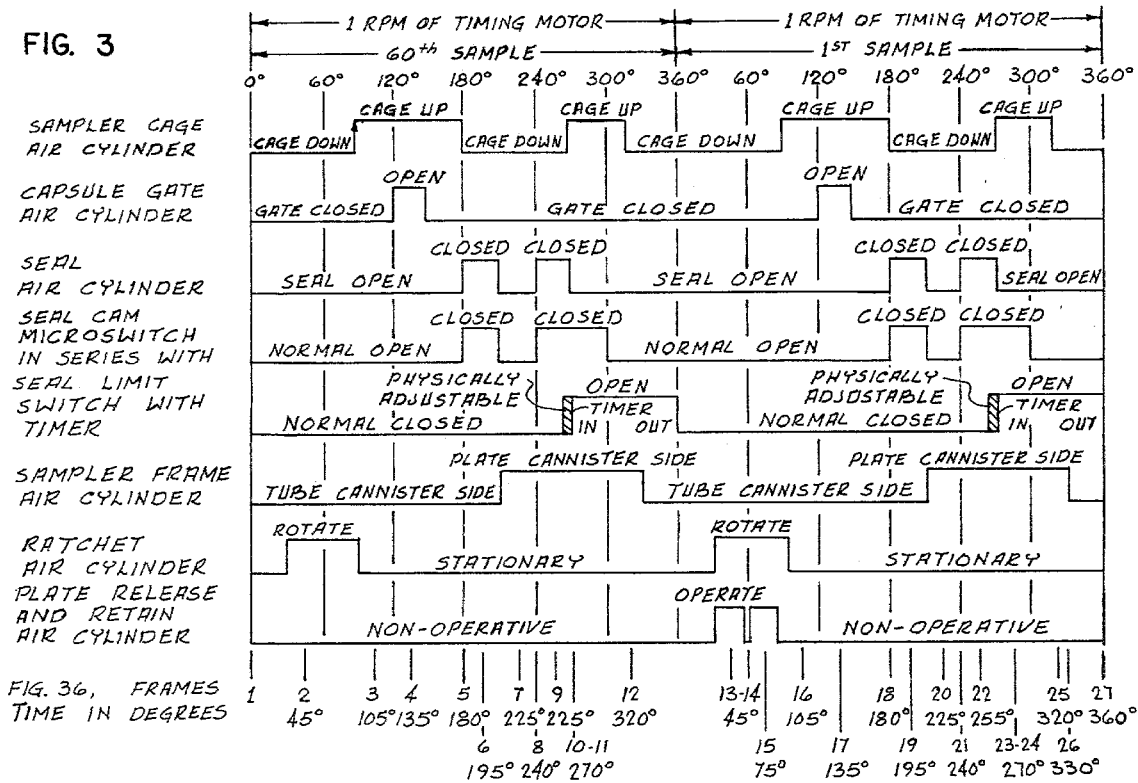
FIG. 3 is a schematic illustrating the timing sequences of the respective components of the sample extractor illustrated in FIG. 2.

Referring now to FIG. 3, which schematically illustrates the operation of various extractor components as a function of the degree of rotation of a 1 rpm timing motor 111, illustrated in FIG. 17, tube canister 15 and plate canister 70 each move 1/60th of one revolution per minute, and make one complete 360° revolution each hour responsive to the activation of 1 rpm timing motor 111. The sampler 40 secures one drilling fluid sample per minute, and each plate 74 is filled with 60 capsules containing drilling fluid samples per hour, and is removed from the plate canister 70 hourly and deposited on the plate conveyor 90, as hereinafter described.

Referring again to FIG. 2 of the drawings, the automatic extractor 11 contains a frame 12, constructed of welded angle iron of sufficient size and strength to provide a sturdy housing or enclosure for the extractor components, and is covered with welded sheet metal 13 of sufficient thickness to withstand rough usage and provide a weatherproof enclosure. All electrical and air supply lines enter the structure through a canopy-covered slot (not illustrated) provided in one side of the enclosure. Access to the air and electrical controls can be provided by means of a weatherproof, hinged door or similar closure means (not illustrated). Capsules 60 serve as storage reservoirs for the drilling fluid samples taken, and are each sealed from loss of fluid or gas by a cap 75, formed in each plate 74. Each one of capsules 60 is machined from suitable bar stock to provide an adequate interior capacity for liquid samples, with a generally hemispherically shaped, closed lower end and an upper end which is characterized by a neck of reduced diameter. Each one of capsules 60 fits easily into cage 58 of cage arm 59, in sampler 40, and the neck diameter is of sufficient size to provide a snug, leak-proof fit in each plate 74 against each cap 75, as further illustrated in FIG. 35. Each cap 75 may be molded of a selected elastomer or other material suitable for sealing purposes, according to the knowledge of those skilled in the art.

Referring to FIGS. 2 and 4-6, tube canister 15 includes a tube top bearing 16, rigidly attached to frame 12, and a tube bottom bearing 27, carried by a support column 26. Suspended vertically between these two bearings is tube shaft 21, which is of sufficient size to provide rotational support for top support plate 20 and bottom support plate 22 of tube canister 15. Top support plate 20 and bottom support plate 22 are preferably machined from hot rolled plate of sufficient thickness to provide rigid support for tubes 17, and are attached to the tube shaft 21 in parallel, horizontal relationship. Tubes 17 are flush-mounted to the exterior surfaces of top support plate 20 and bottom support plate 22, and stand in vertical, parallel relationship to tube shaft 21, in 60 holes drilled in top support plate 20 and bottom support plate 22, respectively. Tubes 17 are cut from tubular stock of sufficient wall thickness to insure the necessary rigidity, and are constructed to provide a sliding fit for each one of capsules 60 stored inside tubes 17 in stacked relationship. Rigidly attached to tube shaft 21 above top support plate 20 is tube timing pulley 19, which is positioned in a horizontal plane with respect to a plate timing pulley 80 mounted in cooperation with plate canister 70. Positioned below and with minimum clearance with respect to bottom support plate 22 of tube canister 15 is stationary base plate 23, which is rigidly attached to support column 26, supported by frame 12. Stationary base plate 23 is preferably also machined from hot rolled plate of sufficient thickness to provide a nonflexible support for the capsules 60 contained in the tubes 17, and the hemispheric lower ends of the bottom ones of capsules 60 positioned in tubes 17 slide across the upper surface of stationary base plate 23 as tube canister 15 is rotated. The diameter of stationary base plate 23 is equal to the diameter of bottom support plate 22, and a capsule gate, hereinafter described, is provided in stationary base plate 23 to allow a single one of capsules 60 to escape from tubes 17 in tube canister 15 by operation of gravity in a selected time interval.

Referring now to FIGS. 12-16 of the drawings, the escape and retention, respectively, of capsules 60 in tubes 17 of tube canister 15 is controlled by a capsule gate 24, which is actuated by a capsule gate air cylinder 25, the latter of which is pivotally attached to frame 12, as illustrated in FIGS. 15 and 16. Capsule gate 24 is machined with a sliding fit in stationary base plate 23, and is of the same height as capsules 60, and is further provided with a vertically oriented gate opening 24c to slidably receive capsules 60. The horizontal interior gate surface 24a of capsule gate 24 is flush with the stationary base plate 23. Capsule gate air cylinder 25 is, in a preferred embodiment, a double-acting air cylinder, and is actuated by the 1 rpm timing motor 111, and drives capsule gate cam 132, as illustrated in FIGS. 3, 17 and 22. Referring again to FIGS. 3 and 22, when capsule gate cam 132 reaches 120° of rotation capsule gate microswitch 133 closes, energizing a capsule gate solenoid valve (not illustrated). The capsule gate solenoid valve is preferably characterized as a four-way, valve-open exhaust-with-solenoid operator having a full spring return, and when it is energized, capsule gate air cylinder 25 is caused to retract, which moves the capsule gate 24 outward and discharges one of the capsules 60, positioned in gate opening 24c, into cage 58, as illustrated in FIGS. 15 and 16. The capsule gate solenoid valve is identical in design to the seal solenoid valve 117, illustrated in FIG. 33. At 150° of rotation of capsule gate cam 132, capsule gate microswitch 133 opens, deenergizing the capsule gate solenoid valve and allowing the spring return to shift the air direction to the opposite side of the piston in the double-acting capsule gate air cylinder 25, causing it to extend, which closes the now empty capsule gate 24. The column of capsules 60 positioned inside one of tubes 17 oriented over gate opening 24c in the closed, empty capsule gate 24 now facilitates release of the lowest one of capsules 60 into the capsule gate 24. The released capsule is confined in capsule gate 24 by capsule retainer 28, and is in position for entry into cage 58 in the next cycle of operation. After discharging a filled one of capsules 60 into contact with a registering cap 75 in a plate 74 of plate canister 70 as hereinafter described, cage 58 returns to a position on the tube canister 15 side of automatic extractor 11 to await further action by capsule gate 24.

Referring again to FIG. 2 of the drawings, the rotational motion of tube canister 15 is effected by means of a timing belt 18, which cooperates with tube timing pulley 19 of tube canister 15, and plate timing pulley 80 of plate canister 70. As heretofore noted, the timing sequence of the tube canister 15 rotation is illustrated in FIG. 3, and at 45°-90° of rotation of 1 rpm timing motor 111, 1/60th of a revolution is achieved by tube canister 15, as illustrated.

Plate canister 70 is suspended vertically from plate top bearing 71, which is rigidly attached to frame 12 by means of hollow plate shaft 72, with the lower end of plate shaft 72 rigidly attached in concentric relationship to shell top 73a of shell 73. Plate timing pulley 80 is carried by plate shaft 72 at a point above shell 73, and above plate timing pulley 80 is positioned a ratchet wheel 83, fitted with ratchet teeth 85, and attached to plate shaft 72. Plate shaft 72 is preferably formed of drilled hot rolled bar stock having a sufficiently thick wall to be extremely rigid. Ratchet wheel air cylinder 84 is rigidly attached to frame 12 and cooperates with ratchet wheel 83 by means of a pawl 81, which engages ratchet teeth 85 and is carried by the piston 86 of ratchet wheel air cylinder 84. A single stroke of ratchet wheel air cylinder 84 effects 1/60 of a revolution of plate canister 70, since ratchet wheel 83 is equipped with 60 ratchet teeth 85, arranged such that one stroke of ratchet wheel air cylinder 83 causes pawl 81 to engage a single tooth of ratchet teeth 85 in ratchet wheel 84. This rotational motion of plate canister 70 is conveyed to tube canister 15 by the action of timing belt 18, as heretofore described.

Figure 6:
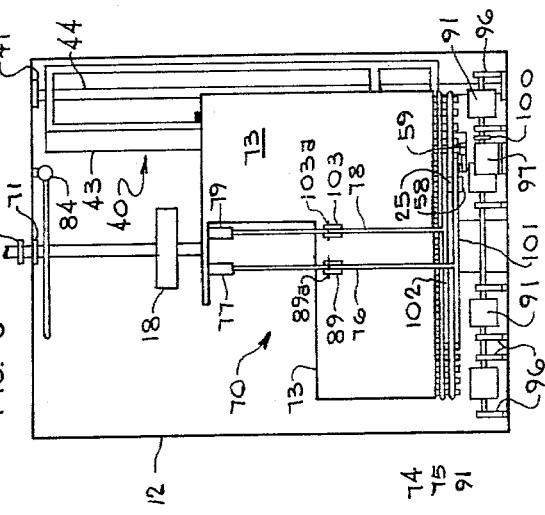
FIG. 6 is a right side elevation of the sample extractor illustrated in FIG. 2, with the end of the cabinet or housing removed.

Referring to FIGS. 2, 6, 28, 29 and 35, shell 73 of plate canister 70 is preferably constructed of hot rolled plate to form a vertically oriented, generally cylindrically-shaped chamber with the bottom end open and an opening provided in the upper half of the chamber of sufficient size to allow a quantity of empty plates 74 to be deposited in the interior of shell 73 for eventual storage of filled capsules 60. Plates 74 are preferably formed from hot rolled plate of sufficient thickness to be rigid, and are characterized by a circular ring with a diameter sufficiently large to facilitate a sliding fit inside shell 73, as shown in FIG. 2. 60 plate holes 88 are drilled in each plate, as illustrated in FIG. 29, to accommodate the caps 75, which seal the filled capsules 60, as illustrated in FIG. 35. A notch 87, provided in the outer circumference of plates 74 as illustrated in FIGS. 28 and 29, is designed to ride a vertically mounted guide rod (not illustrated) located inside shell 73 to position each plate 74 in a configuration to properly receive filled capsules 60 deposited by cage 58. Hemispheric shell top 73a is welded to the shell 73, which insures rigidity and allows plate release air cylinder 77 and plate retaining air cylinder 79 to be suspended vertically from shell top 73a in the interior of shell 73, as illustrated in FIGS. 2 and 6 of the drawings.

Referring now to FIGS. 2, 6, 24 and 25, the two plate release cranks 76 are made of bar stock of sufficient size to insure rigidity, and are pivotally attached to the opposite sides of the exterior vertical walls of shell 73 by a pair of release clevis 89 and release clevis pins 89a, as illustrated in FIGS. 2, 24 and 25. To the lower end of plate release cranks 76 is welded lower collars 101, which in closed position support the lowest one of stacked plates 74. The piston of plate release air cylinder 77 is attached to the upper end of plate release cranks 76 by means of crank slots 76a and cylinder pins 77a. A downward stroke of plate release air cylinder 77 causes lower collars 101, attached to plate release cranks 76, to open outwardly, as illustrated in FIG. 25, and allows the lowest plate 74 to drop onto plate conveyor 90. An upward stroke of plate release air cylinder 77 returns plate release cranks 76 and lower collars 101 to the closed position, as illustrated in FIG. 24. Similarly, plate retaining air cylinder 79 is suspended vertically from shell top 73a opposite plate release air cylinder 77, as illustrated in FIG. 6. Plate retaining cranks 78, formed of bar stock of sufficient size to insure rigidity, are pivotally attached to opposite sides of the exterior vertical walls of shell 73 adjacent plate release cranks 76 by two retaining clevis 103 and retaining clevis pins 103a. To the lower end of plate retaining cranks 78 is welded a pair of upper collars 102, which in closed position support the stack of plates 74 inside shell 73, with the exception of the bottom plate 74, which is supported by lower collars 101 and plate release cranks 76 while lower collars 101 are in the closed position, as illustrated in FIGS. 2 and 24. The piston of plate retaining air cylinder 79 is attached to the upper end of plate retaining cranks 78, and a downward stroke of plate retaining air cylinder 79 causes upper collars 102 to open outwardly, and permits the stack of plates 74 inside plate canister 70 to drop downwardly onto lower collars 101. An upward stroke of plate retaining air cylinder 79 returns plate retaining cranks 78 to the closed position, and upper collars 102, positioned on the lower end of plate retaining cranks 78, fit between the two bottom plates 74 such that they again support the stack of plates 74 with the exception of the lowest plate. Accordingly, activation of plate release air cylinder 77 always permits only the lowest plate in the stack of plates 74 to drop onto belt 91 of plate conveyor 90.

Each cap 75 protrudes below the bottom surface of plates 74 as illustrated in FIG. 35, and each plate is separated from the adjoining plate by the thickness of the protrusion of cap 75, thus allowing upper collars 102, attached to plate retaining cranks 78, sufficient mechanical operating room. Plate retaining cranks 78 also serve as an upward restraining force on the lowest one of plates 74 when cage 58, provided with a full capsule 60, forces the capsule into a registering cap 75 in the plate. It will be appreciated that plate release cranks 76 and plate retaining cranks 78 are alternately opened and closed, as hereinafter described.

Referring now to FIGS. 2, 30, 31 and 32, in the retention and release of plates 34 in plate canister 70, the piston 86 in plate release air cylinder 77 is caused to extend when cam operator wheel 137 of plate release cam operator 129, (rigidly attached to shell 73) engages plate release cam 128, which is attached to frame 12, as illustrated in FIGS. 30, 31 and 32, responsive to rotation of plate canister 70. Plate release cam 128 contacts cam operator wheel 137 of plate release cam operator 129 and actuates plate release 4-way valve 130, mounted on shell 73, which supplies air from an external air supply 135 through rotating union 131 and plate shaft 72 to plate release air cylinder 77, as illustrated in FIG. 30. This action removes lower collars 101 from contact with the bottom one of plates 74, and allows the loaded plate to drop onto plate conveyor 90. When plate release cam operator 129 disengages from plate release cam 128, plate release 4-way valve 130 switches, and piston 86 in plate release air cylinder 77 retracts, causing plate release cranks 76 and lower collars 101 to move inwardly. The plate release cam 128 cycle is illustrated in FIG. 3, and is completed before the plate retainer cam 125 cycle, which is essentially the same as the plate release cam 128 cycle except in an out-of-phase relationship and hereinafter described, is begun. Plate retainer cam 125 is also rigidly attached to frame 12 as illustrated in FIG. 31, and when it is contacted by cam operator wheel 137 of plate retaining cam operator 126, the shell-mounted plate retaining 4-way valve 127 switches, causing plate retaining air cylinder 79 to extend, forcing plate retaining cranks 78 and upper collars 102 outward, releasing the stacked plates 74 inside shell 73 and allowing them to drop onto lower collars 101 of plate release cranks 76. When plate retaining cam operator 126 disengages from plate retaining cam 125, the 4-way valve 127 again switches, causing double-acting plate retaining air cylinder 79 to retract, and closing upper collars 102 between the two bottom plates 74. This alternate open-close operation of the plate release and plate retaining mechanisms occurs after the 60th sample capsule is deposited in one of plates 74, and before the first sample of the new bottom one of plates 74 is deposited in the respective cap 75, as illustrated in FIG. 3.

Referring now to FIGS. 2, 30, and 32, as heretofore described, air is supplied to plate release 4-way valve 130 from an external air supply 135, through the hollow upper portion of plate shaft 72, by means of a rotating union 131, which is carried by the upper end of plate shaft 72, as illustrated in FIG. 30. Plate retaining 4-way valve 127 cooperates in similar manner with plate shaft 72, and air is routed from air supply 135 through the rotating union 131, down the hollow interior of plate shaft 72, and exits from a side outlet in plate release 4-way valve 130 and plate retaining 4-way valve 127, which are both spring-loaded for return action. Plate release 4-way valve 130 and plate retaining 4-way valve 127 in turn supply air to the double-acting plate release air cylinder 77 and plate retaining air cylinder 79, respectively.

Referring to FIGS. 3 and 17-23, tube canister 15 and plate canister 70 are rotated according to the timing sequence of 1 rpm timing motor 111, which is illustrated in FIG. 17. This timing sequence is shown in FIG. 3 as follows: when ratchet cam 122, illustrated in FIG. 21, reaches 30° of rotation, ratchet microswitch 123 (normally open as illustrated in FIGS. 17 and 21), closes, energizing ratchet solenoid valve 124 (a four-way, valve-open exhaust-with-solenoid operator with full spring return), which causes ratchet wheel air cylinder 84 (a double-acting air cylinder) to extend, turning ratchet wheel 83 and plate canister 70 1/60th of one revolution. At 90° of rotation of ratchet cam 122, ratchet microswitch 123 opens, deenergizing ratchet solenoid valve 124, and allowing the full spring return to shift the flow of air to the opposite side of the piston. This action causes ratchet air cylinder 84 to retract, allowing pawl 81 to seat in a new tooth position in ratchet teeth 85, ready for the next 1/60th of one revolution stroke. Plate canister 70 is restrained from reversing in movement by its own weight and by the added weight of tube canister 15, to facilitate rotation only in one direction. In a preferred embodiment of the invention 1 rpm timing motor 111 and the cams and microswitches associated with the motor are located in a conveniently located command center 110, as illustrated in FIG. 23.

Figure 5:
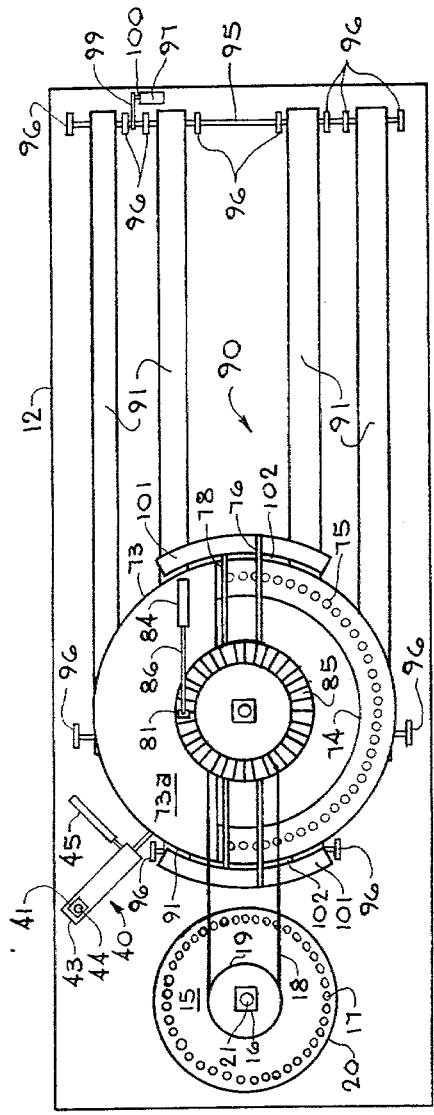
FIG. 5 is a top elevation of the sample extractor illustrated in FIG. 2, with the top of the cabinet or housing removed.
Figure 4:
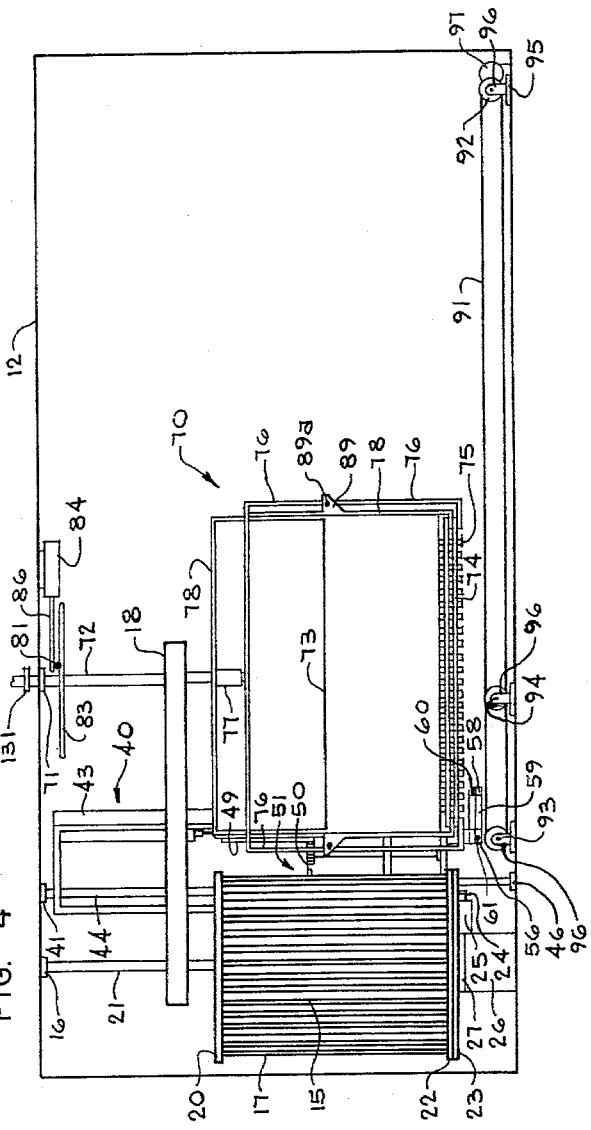
FIG. 4 is a front elevation of the sample extractor illustrated in FIG. 2, with the front side of the cabinet or housing removed.

Referring now to FIGS. 2 and 4-6, plate conveyor 90 includes 4 belts 91, carried by pulleys 92 and driven from a single drive motor 97, by means of a v-belt 100. A drive v pulley 98 is carried by drive motor 97 and cooperates with v-belt 100 and a driven v pulley 99, which is positioned on 4-pulley shaft 95 at one end of plate conveyor 90. 4-pulley shaft 95 is supported by pillow bearings 96, attached to frame 12, as illustrated in FIG. 5. Alternatively, the pulleys and 4-pulley shaft 95 can be supported and arranged as illustrated in FIG. 34, with 4-pulley shaft 95 supported by a single pair of pillow bearings 96. A short, 2-pulley shaft 93, supported by additional pillow bearings 96, and a long, 2-pulley shaft 94, supported by more pillow bearings 96, are also attached to frame 12 at the opposite end of plate conveyor 90, as illustrated in FIGS. 2 and 4. With drive motor 97 in continuous operation, and when one of plates 74 is released from plate canister 70 by the action of plate release cranks 76 and lower collars 101, belts 91 carry the released one of plates 74 to an area which is clear of the next plate to be ejected.

Referring now to FIGS. 7-11 of the drawings, sampler 40 includes a sampler frame 43 of welded steel construction and of sufficient strength to provide rigid vertical and rotational support for the various components mounted therein. Sampler shaft 44 is vertically mounted between sampler top bearing 41 and sampler bottom bearing 46, which are both attached to frame 12. Sampler frame 43 is pinned to sampler shaft 44 in order to permit free rotation of sampler frame 43 with respect to frame 12. Outer barrel guide crank shaft 47 is rotationally and vertically supported at its lower end in outer barrel guide crank shaft lower bearing 63, which is carried by sampler frame 43. The upper portion of outer barrel guide crank shaft 47 is rotationally and vertically supported by outer barrel guide crank shaft upper bearing 64, which is also rigidly attached to sampler frame 43. To the upper end of outer barrel guide crank shaft 47 is attached outer barrel guide crank 51, fitted with gear teeth 67, which are positioned in rotational contact with slotted outer barrel guide rail 49, vertically attached to an outer barrel 48, such that outer barrel guide rail 49 and the gear teeth 67 of outer barrel guide crank 51 mesh in contact. Outer barrel 48 is rigid and tubular in shape, and is exterior to, and forms a concentric, sliding fit over inner barrel 53, the latter of which is machined in cylindrical configuration, preferably from roll stock. The upper end of inner barrel 53 is male threaded to receive the female thread of upper retainer 52, which is attached to the clevis end of the vertically mounted sampler air cylinder 42, suspended in sampler frame 43 at the upper interior end. The lower portion of inner barrel 53 is male threaded to receive the female thread of lower retainer 56. When outer barrel 48 is fitted concentrically and slidably over inner barrel 53, and upper retainer 52 and lower retainer 56 are attached to inner barrel 53, there is effected a rotational fit between inner barrel 53 and outer barrel 48. Lower retainer 56 vertically supports outer barrel 48. A window 65 is provided in the upper portion of outer barrel 48, as illustrated in FIG. 7, and inner barrel rail 55 projects through window 65, and is rigidly attached to inner barrel 53. A sliding fit contact exists between inner barrel guide 54, which is vertically attached to the inside of sampler frame 43, and inner barrel rail 55. As illustrated in FIG. 7, the lower portion of inner barrel 53 is provided with horizontally disposed grooves 66 at three points to receive O-rings 62, which serve as a seal between inner barrel 53 and outer barrel 48 when these members are submerged in the drilling fluid. A cage arm 59 is attached to lower retainer 56, and cage arm 59 carries cage 58 in order to provide a vertical receptacle for capsules 60. In a preferred embodiment of the invention, retainer set screws 61 serve to lock upper retainer 52 and lower retainer 56 to inner barrel 53. Frame air cylinder 45 is pivotally attached to frame 12 and sampler frame 43, and provides rotational motion of sampler 40 about the vertical axis of sampler shaft 44 to move cage 58 from the tube canister 15 side of sample extractor 11 to the plate canister 70 side of the extractor, as illustrated in FIG. 7. A seal 57 is attached to outer barrel 48 and serves to seal and unseal capsules 60 in cage 58 by action of seal air cylinder 50, which is pivotally attached to sampler frame 43 and outer barrel guide crank 51, as illustrated in FIG. 9. This action is shown with related components more particularly in FIGS. 26 and 27. When one of capsules 60 enters empty cage 58, in due course it is temporarily topped with seal 57 by action of seal air cylinder 50 before being submerged in the drilling fluid by the extension of sampler air cylinder 42, as illustrated in FIG. 10. Once submerged, seal 57 opens by action of seal air cylinder 50, and permits fluid to enter the empty capsule. Upon retraction of seal air cylinder 50 responsive to contraction of sampler air cylinder 42, seal 57 subsequently covers the capsule before the capsule is withdrawn from the drilling fluid after sampler frame 43 moves from the tube canister 15 side of automatic extractor 11 to the plate canister 70 side by action of frame air cylinder 45. As the sealed one of capsules 60 is withdrawn from the fluid to a position directly under an empty cap 75 in the bottom plate 74 of plate canister 70, seal 57 is again rotated by action of seal air cylinder 50, as illustrated in FIGS. 27 and 33, just prior to contact of the capsule with cap 75. Continued upward motion of the capsule forces the neck of the capsule into the cap 75. As sampler air cylinder 42 extends, cage 58 moves downwardly, leaving the capsule suspended, stalagtite fashion, from cap 75 in the bottom one of plates 74 of plate canister 70. This action of sampler 40 is controlled by 1 rpm timing motor 111 and related cam movements, as hereinafter described.

Referring now to FIGS. 3 and 17–22, in a preferred embodiment of the invention 1 rpm timing motor 111 is a 1 rpm programming cam timer having 5 cams which operate 5 microswitches, which microswitches in turn energize 5, 4-way-valve-open exhaust-solenoid operators with full spring returns, such as those illustrated in FIGS. 32 and 33, to control the air supply to 5 double-acting air cylinders. The operation of three of these air cylinders with respect to the 0° to 360° position of its respective cam is as follows: Sample air cylinder 42 controls the vertical movement of cage 58 through sampler cam 112 contact with sampler cam microswitch 113, as illustrated in FIG. 18, and when sampler cam 112 is in the 0° to 90° position, cage 58 is down; when in the 90° to 180° position, cage 58 is up; when in the 180° to 270° position, cage 58 is down; when in the 270° to 315° position, the cage 58 is up; and when in the 315° to 360° position, cage 58 is down, and the cycle is complete, as illustrated in FIG. 3. A sampler solenoid valve (not illustrated) is characterized by a 3-way, 2 position, single solenoid, spring pneumatic control valve, and when normally on sampler microswitch 113 closes, the sampler solenoid valve is energized, and air flows to one side of the double-acting sampler air cylinder 42, the shaft extends, and cage 58 is submerged in the drilling fluid; when sampler microswitch 114 returns to its normal position, the sampler solenoid valve is deenergized and the spring return allows the air to flow to the opposite side of double-acting sampler air cylinder 42, the shaft retracts, and cage 58 rises from the drilling fluid. The sampler solenoid valve is identical in design to the seal solenoid valve 117, illustrated in FIG. 33. Seal air cylinder 50 controls the sealing and unsealing of each one of capsules 60 in cage 58 through seal cam 115 contact with seal microswitch 116, as illustrated in FIG. 19. Consequently, as shown in FIG. 3, when seal cam 115 is in the 0° to 180° position, seal 57 is open; from 180° to 210°, seal 57 covers the capsule in cage 58; from 210° to 240°, seal 57 uncovers the capsule, allowing drilling fluid to enter the capsule; from 240° to 270°, seal 57 again covers the capsule as the capsule is withdrawn from the drilling fluid. Because seal 57 must open at the proper time to allow the capsule to enter cap 75 in each respective one of plates 74 and remain open to allow the capsule to escape, a premature closing of seal 57, upon contact by cage 58 with seal limit switch with timer 118, which is rigidly attached to frame 12 is prevented, since seal 57 opens upon contact and does not close until the timer times out; but at this time seal 57 stays open as the cage 58 returns to the tube canister 15 side of sample extractor 11. Similarly, frame air cylinder 45 controls the position of sampler 40 by the action of a frame cam 110 contact with frame microswitch 120, as illustrated in FIG. 20. A similar switching mechanism is provided for plate release air cylinder 77 and plate retainer air cylinder 79, as heretofore described.

It will be appreciated by those skilled in the art that the purpose of this invention is to offer a method and apparatus which is not presently available to secure multiple individual, identifiable, sealed capsule samples of drilling fluid after the drilling fluid reaches the surface, which samples can be stored and analyzed at will as to hydrocarbon and other components by currently available techniques. Accordingly, the desired samples can be acquired by using the above described apparatus as follows: In operation, and referring again to FIG. 36, at the moment of activation of 1 rpm timing motor 11 the motor rotation is at 0°, and as shown in frame 1 of FIG. 36, the cage 58 is empty and submerged in the drilling fluid with seal 57 in the open position. At this point in time it will be assumed that the bottom one of plates 74 in plate canister 70 contains fifty-nine samples. When 1 rpm timing motor 111 advances to 45°, as shown in frame 2, the cage is still empty and submerged, with seal 57 open. The plate canister 70 is rotated 1/60 of one revolution responsive to the action of ratchet wheel air cylinder 84 as heretofore described, which positions the bottom one of plates 74 to receive the sixtieth capsule 60. Furthermore, tube canister 15 also moves 1/60 of a revolution by action of timing belt 18, which insures uniform withdrawal of the capsules 60 from within the tube canister 15, as heretofore described. When 1 rpm timing motor 111 advances to 105° of rotation, and as shown in frame 3 of FIG. 36, cage 58 is empty and is rising vertically from immersion in the drilling fluid into loading position beneath capsule gate 24 and tube canister 15, with seal 57 open, responsive to the action of sampler air cylinder 42. Upon rotating to the 135° position, and as shown in frame 4, 1 rpm timing motor 111 causes capsule gate 24 to open, allowing an empty capsule 60 to slide from within the registering one of tubes 17 in tube canister 15 with gate opening 24c, through gate opening 24c, and into cage 58, which is in stationary position under tube canister 15 with seal 57 in the open position. When 1 rpm timing motor 111 advances to the 180° position, and as shown in frame 5 of FIG. 36, cage 58 and the empty capsule 60 therein are moving downwardly into the drilling fluid with the seal 57 in closed configuration, the closing of seal 57 being actuated by seal air cylinder 50, in order to prohibit premature entry of fluid into the capsule 60 at this point in the immersion sequence. When 1 rpm timing motor 111 advances to the 195° position, as shown in frame 6 of FIG. 36, cage 58 contains a sealed, empty capsule 60 which is fully submerged in the fluid and is positioned on the tube canister 15 side of the automatic extractor 11. Upon reaching 225° of rotation, and as shown in frame 7, 1 rpm timing motor 111 causes cage 58 to be rotated to the plate canister side of automatic extractor 11 by action of frame air cylinder 45 as heretofore described. At this point in the sample capture sequence seal 57 has been opened by action of seal air cylinder 50 for a sufficiently long period of time to allow fluid to enter the previously sealed capsule. At 240° of rotation of 1 rpm timing motor 111, and as shown in frame 8, cage 58 is still submerged in the drilling fluid stream at a point beneath plate canister 70, immediately prior to closure of seal 57. Upon reaching 255° of rotation of 1 rpm timing motor 111, and as shown in frame 9, seal 57 has closed on the capsule 60 positioned in cage 58, responsive to the action of seal air cylinder 50. When the timing motor rotation reaches 270°, cage 58 is emerging from the fluid with seal 57 still in closed position on the capsule 60, as illustrated in frame 10 of FIG. 36.

When 1 rpm timing motor 111 reaches 270°±1° of rotation as shown in frame 11, cage 58, containing a filled capsule 60, has contacted seal limit switch with timer 118. This contact causes seal air cylinder 50 to open seal 57 just prior to entry of the capsule 60 into the last unoccupied cap 75 in the bottom one of plates 74 in plate canister 70, by continued upward movement of sampler air cylinder 42, as illustrated in FIGS. 10 and 33. Referring again to FIGS. 3 and 36, when 1 rpm timing motor 111 reaches 320° of rotation, and as shown in frame 12 of FIG. 36, empty cage 58 is descending vertically with seal 57 still in the open position by action of the timer circuit contained in the seal limit switch with timer 118, which prohibits seal 57 from prematurely closing. The bottom one of plates 74 is now filled with 60 capsules and is ready to be ejected. Ejection of the filled bottom plate 74 automatically occurs responsive to contact between cam operator wheels 137 of plate release cam operator 129 and plate release cam 128, respectively, to activate plate release 4-way valve 130 and plate release air cylinder 77, as heretofore described. This action causes lower collars 101 to move outwardly from contact with the bottom one of plates 74 to deposit the plate on belts 91 of plate conveyor 90, as illustrated in FIG. 2. When the bottom and loaded one of plates 74 is released from plate canister 70, continued operation of 1 rpm timing motor 111 effects continued rotation of plate canister 70 through the operation of ratchet wheel 83 and associated mechanisms, as heretofore described, and upper collars 102 are deflected outwardly responsive to the action of plate retaining air cylinder 79 and plate retaining 4-way valve 127, to again deposit an empty plate on lower collars 101.

Referring again to FIGS. 3 and 36 of the drawings, when 1 rpm timing motor 111 has advanced again to 45° of rotation as shown in FIG. 3 and frame 13, an empty cage 58 is again fully submerged in the drilling fluid with seal 57 remaining open, since seal microswitch 116 has moved to the open position before the seal limit switch with timer 118, with which it is in series, has "timed out" and closed. Plate canister 70 is rotated 1/60 of a revolution and the plate release cam operator 129, as part of the plate release 4-way valve 130, as shown in FIGS. 30 and 31, engages the plate release cam 128 attached to main frame 12, which again actuates plate release 4-way valve 130, causing the plate release air cylinder 77 to extend and move the plate release crank 76 outward, which causes the lower plate 74 to drop. When the timing motor rotation has reached 45°±1°, and as shown in frame 14 of FIG. 36, plate release cam operator 129 has disengaged from plate release cam 128 and the plate release 4-way valve 130, which is spring loaded, has again shifted, causing plate release air cylinder 77 to retract and return plate release crank 76 and lower collars 101 to the inward position to support the new one of empty plates 74 about to be released, as shown in frame 15. Simultaneously, the released plate containing the sixty samples of drilling fluid in sealed capsules 60 is being removed by the plate conveyor 90.

Figure 36:
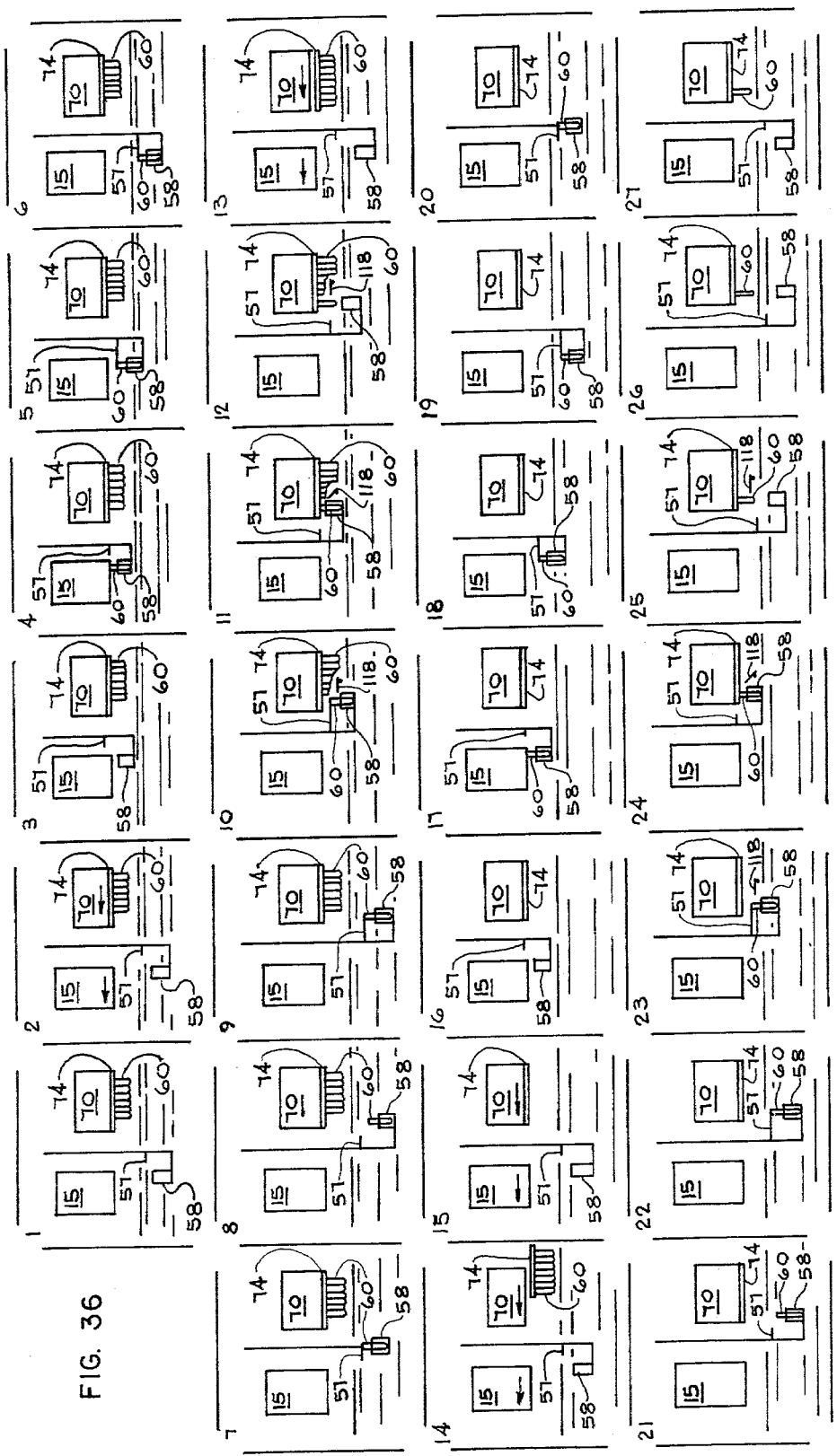
FIG. 36 is a sequence diagram illustrating the various positions of the sampler as a function of the timing motor operation.

As further illustrated in FIG. 3, when the timing process is at 75°, and as shown in frame 15 of FIG. 36, empty cage 58 is fully submerged in the drilling fluid with seal 57 in open position. Plate canister 70 is rotated 1/60 of a revolution, and cam operator wheel 137 of plate retainer cam operator 126, as part of plate retaining 4-way valve 127, engages plate retaining cam 125, attached to main frame 12. This movement activates plate retaining 4-way valve 127, causing plate retaining air cylinder 79 to extend and move plate retaining crank 78 outward, which allows the stack of empty plates 74 contained inside shell 73 to drop onto lower collars 101. As the rotational cycle of plate canister 70 moves to 90° of rotation of 1 rpm timing motor 111, as shown in FIG. 3, plate retaining cam operator 126 has disengaged from plate retaining cam 125, and the springloaded plate retaining 4-way valve 127, has shifted, causing plate retaining air cylinder 79 to retract and return upper collars 102 to an inward position between the lowest one of plates 74 and the second lowest plate, to which support all of plates 74 except the bottom plate, and serves as a restraining force with reference to the bottom plate each time one of capsules 60 is inserted in a cap 75.

When 1 rpm timing motor 111 reaches 105° of rotation, and as shown in frame 16 of FIG. 36, the mechanism is performing identically to the sequence shown in frame 3 of FIG. 36. The lowest one of plates 74 in plate canister 70 is empty of fluid samples as the cycle of filling the bottom plate has begun anew. When the timing motor rotation reaches 330°, and as shown in frame 26 of FIG. 36, empty cage 58 has completed its descent into the drilling fluid by the action of sampler air cylinder 42, and is poised to switch from the plate canister 70 side to the tube canister 15 side of automatic extractor 11, by action of frame air cylinder 45. When 1 rpm timing motor 111 reaches 360°, or 0° of rotation, and as shown in frame 27 of FIG. 36, which is the same as frame 1 (excluding the number of capsules 60 filled with drilling fluid samples which lower plate 74 contains) the sampling cycle is completed for one sample.

Having described my invention with the particularity set forth above, what is claimed is:

1. An automatic extractor for extracting drilling fluid samples from a stream of drilling fluid comprising:
    (a) a vertically oriented tube canister fitted with multiple tubes that internally provided in said tube canister for storing a quantity of empty sample capsules;
    (b) a plate canister positioned in close proximity to said tube canister and a plurality of plates stacked in said plate canister for receiving a quantity of said sample capsules containing said fluid samples;
    (c) a sampling device positioned in pivotal relationship between said tube canister and said plate canister for automatically removing said empty sample capsules from said tubes, immersing said empty sample capsules in said stream of drilling fluid to extract said fluid samples, and positioning said sample capsules containing said fluid samples in said plurality of plates positioned in said plate canister; and (d) timing means for causing release of said empty sample capsules to said sampling device, lowering said sampling device to immerse said sample capsules, pivoting said sampling device beneath said plates, and loading said sample capsules in said plates.

2. The automatic extractor of claim 1 wherein said timing means is a timing motor and a plurality of cams, microswitches, valves and air cylinders cooperating with said timing motor and said tube canister, said plate canister and said sampling device.

3. The automatic extractor of claim 1 further comprising a tube timing pulley carried by said tube canister and a plate timing pulley carried by said plate canister, and a timing belt cooperating with said tube timing pulley and said plate timing pulley to coordinate rotation of said tube canister and said plate canister to facilitate individual extraction of said empty sample capsules from said tube canister and individual loading of said sample capsules filled with said drilling fluid in said plate canister by said sampling device.

4. The automatic extractor of claim 1 further comprising conveyor means positioned beneath said plate canister for removing said plates when said plates are filled with said sample capsules and said sample capsules are ejected from said plate canister.

5. The automatic extractor of claim 1 further comprising:
(a) a tube timing pulley carried by said tube canister and a plate timing pulley carried by said plate canister, and a timing belt cooperating with said tube timing pulley and said plate timing pulley to coordinate rotation of said tube canister and said plate canister to facilitate individual extraction of said empty sample capsules from said tube canister and individual loading of said sample capsules filled with said drilling fluid in said plate canister by said sampling device; and
(b) conveyor means positioned beneath said plate canister for removing said plates when said plates are filled with said sample capsules and said sample capsules are ejected from said plate canister.

6. The automatic extractor of claim 5 wherein said timing means is a timing motor and a plurality of cams, microswitches, valves and air cylinders cooperating with said timing motor and said tube canister, said plate canister and said sampling device.

7. The automatic extractor of claim 1 further comprising plate handling means cooperating with said plate canister for periodically shifting said plates and releasing the bottom one of said plates when the bottom one of said plates is filled with said sample capsules containing said drilling fluid.

8. The automatic extractor of claim 1 further comprising;
(a) a tube timing pulley carried by said tube canister and a plate timing pulley carried by said plate canister, and a timing belt cooperating with said tube timing pulley and said plate timing pulley to coordinate rotation of said tube canister and said plate canister to facilitate individual extraction of said empty sample capsules from said tube canister and individual loading of said sample capsules filled with said drilling fluid in said plate canister by said sampling device;
(b) conveyor means positioned beneath said plate canister for removing said plates when said plates are filled with said sample capsules and said sample capsules are ejected from said plate canister; and
(c) plate handling means cooperating with said plate canister for periodically shifting said plates and releasing the bottom one of said plates when the bottom one of said plates is filled with said sample capsules containing said drilling fluid.

9. The automatic extractor of claim 8 wherein said timing means further comprises a timing motor and a plurality of cams rotationally carried by said timing motor; a plurality of microswitches sequentially activated by the rotation of said cams; a plurality of valves cooperating with said microswitches and caused to open and close responsive to rotation of said cams and activation of said microswitches, respectively; and a plurality of air responsive cylinders carried by said tube canister, said plate canister and said sampling device for activating said plate handling means, rotating said plate timing pulley and operating said sampling device responsive to the rotation of said cams.

10. A method of extracting sealed, encapsulated samples of oil well drilling fluid comprising:
(a) loading empty sample capsules into a sampling mechanism;
(b) immersing said empty sample capsules in a stream of said fluid;
(c) sealing said sample capsules when said sample capsules contain a desired quantity of said fluid and while said sample capsules are immersed in said fluid; and
(d) removing said sample capsules from said fluid.

11. The method of claim 10 further comprising automatically loading said empty sample capsules into said sampling mechanism and automatically unloading said sample capsules from said sampling mechanism.

12. The method of claim 10 further comprising automatically storing said sample capsules.

13. The method of claim 10 further comprising automatically loading said empty sample capsules into said sampling mechanism; automatically unloading said sample capsules from said sampling mechanism and automatically storing said sample capsules.

14. A method of automatically extracting sealed, encapsulated samples of oil well drilling fluid comprising:
(a) sequentially and automatically loading individual, empty sample capsules having open tops into a sampling mechanism;
(b) automatically immersing said empty capsules individually in a stream of said fluid for a sufficient length of time to substantially fill said capsules with a quantity of said fluid;
(c) automatically temporarily sealing said open tops of said capsules while said capsules are submerged in said drilling fluid; and
(d) automatically removing said capsules from said drilling fluid.

15. The method of claim 14 further comprising automatically inserting said capsules individually and sequentially in a storage container which forms a sealed cap on said open tops of said capsules after said capsules have been removed from said drilling fluid.

16. A method of automatically extracting a plurality of sealed encapsulated samples of oil well drilling fluid comprising:

(a) loading a supply of empty sample capsules having open tops in a capsule supple means;

(b) automatically transferring said empty sample capsules sequentially into a sampling mechanism;

(c) automatically immersing said empty sample capsules in a stream of said drilling fluid for a sufficient length of time to substantially fill said capsules with a quantity of said drilling fluid;

(d) automatically temporarily sealing said open tops of said capsules while said capsules are submerged in said drilling fluid;

(e) automatically removing said capsules from said drilling fluid and storing said capsules in a capsule storage means.

17. The method of claim 16 wherein said capsules are automatically, individually and sequentially transferred to said sampling mechanism, filled with said drilling fluid, and stored in said capsule storage means.

* * * * *